(12) United States Patent
Sumi (10) Patent No.: US 6,420,145 B1
(45) Date of Patent: Jul. 16, 2002

(54) YUNNAN SL-001 STRAIN (75) Inventor: Hiroyuki Sumi, Okayama (JP)

(73) Assignee: Honda Trading Corporation (JP)

(*) Notice: Subject to any disclaimer, the term of this patent is extended or adjusted under 35 U.S.C. 154(b) by 0 days.

(21) Appl. No.: 09/831,092

(22) PCT Filed: Nov. 16, 1999

(86) PCT No.: PCT/JP99/06380

§ 371 (c)(1),
(2), (4) Date: May 3, 2001

(87) PCT Pub. No.: WO01/36591

PCT Pub. Date: May 25, 2001

(51) Int. Cl.[7] .............................. C12P 7/26; C12N 1/20
(52) U.S. Cl. ..................................... 435/148; 435/252.5
(58) Field of Search ................................ 435/252.5, 148

(56) References Cited

FOREIGN PATENT DOCUMENTS

| JP | 8-009916 | 1/1996 |
| JP | 8-019378 | 1/1996 |
| JP | 8-073396 | 3/1996 |

OTHER PUBLICATIONS

Article: Production of Water–Soluble Vitamin K by Okara Fermentation, Hiroyuki Sumi et al., Nippon Nogeikagaku Kaishi vol. 73, No. 6, pp. 599–604, 1999.

*Primary Examiner*—Herbert J. Lilling
(74) *Attorney, Agent, or Firm*—Baker & Daniels (57) ABSTRACT

The present invention provides a microorganism capable of producing vitamin K or a derivative thereof with good efficiency. The present invention relates to Yunnan strain SL-001 FERM BP-6713, a new strain belonging to *Bacillus subtilis*.

11 Claims, 4 Drawing Sheets

YUNNAN SL-001 STRAIN

This application is a 371 of PCT/JP99/06380 filed Nov. 16, 1999.

TECHNICAL FIELD

The present invention relates to a new strain of *Bacillus subtilis*. More specifically, the present invention relates to a *Bacillus subtilis* strain capable of efficiently producing vitamin K or a derivative thereof.

BACKGROUND ART

Heretofore, vitamin K is known to be an factor necessary for blood clotting or coagulation. Vitamin K is one of the fat-soluble vitamins and also called "antihemorrhagic vitamin" since the deficiency in vitamin K causes reduced coagulability of blood. It has been recently suggested that the reduced coagulability of blood may be caused by the deficiency of vitamin K since vitamin K is essential for the biosynthesis of several blood clotting factors including prothrombin. However, occurrence of vitamin K deficiency is rare, since only a minute amount of vitamin K of the order of $\mu g$ is required for preventing the reduction in coagulability of blood in a living body and vitamin K is usually supplied from intestinal bacteria in an adult human. Synthetic vitamin $K_1$ or $K_2$ has been used as a therapeutic for the treatment of vitamin K deficiency hemorrhagic disease, and a natural vitamin $K_1$ concentrate has been used as a food for preventing the condition. Hence, vitamin K has been received less attention.

In recent years, however, it has become evident that vitamin K has both bone formation stimulative effect and bone resorption inhibitive effect and the administration of vitamin K can increase the bone density. On the other hand, osteoporosis is a condition characterized by brittleness of bone caused by aging, diseases or the like and associated with fracture or severe pain. Osteoporosis is being emerged as a major social problem from the viewpoint of medical care of the aged. It has been reported that patients with osteoporosis have a blood vitamin K level of about one-half that observed in normal individuals. In view these facts, synthetic vitamin K has been put in clinical tests as a therapeutic for osteoporosis. However, unlike the case of hemorrhagic disease, clinical tests demonstrate that, for the treatment and prevention of osteoporosis, administration of vitamin K in an amount as large as at least 45 mg per day is necessary for effective agglomeration of bone mass. For osteoporosis, prevention is more important than treatment after developing its symptoms. Therefore, it is desired to intake vitamin K through food on a day-to-day basis. However, it is yet unknown what amount of vitamin K should be taken by a normal individual per day for increasing the bone mass and for effective prevention of osteoporosis. Moreover, it seems to be difficult to take in such an amount of vitamin K as mentioned above through existing foods.

As mentioned above, it is desirable to take vitamin K through daily foods. In fact, vitamin $K_1$ can be taken through green/yellow vegetables and seaweeds, and vitamin $K_2$ can be taken through fermented foods such as "natto" (a slippery fermented soybeans). However, if 45 mg of vitamin K (which is the amount reported to be effective for amelioration of osteoporosis) is taken through commercial foods, for example for a food containing 1 ppm of vitamin K, a large amount of 45 kg per day of the food should be taken, which is actually very difficult. A food which is most rich in vitamin K among the existing foods is natto, which contains a dozen ppm of vitamin K. However, even natto should be eaten in a large amount of several hundreds grams to several kilograms daily. It seems to be difficult to eat such a large amount of natto every day, from the viewpoint of liking. In addition, when vitamin K is orally taken in a single-shot manner, sufficient effect cannot be obtained due to the short half-life of vitamin K. In contrast, intake of a large amount of vitamin K at a time may cause a problem of adverse side-effects. Therefore, it is desirable to take vitamin K in a concentrated form. However, commercially available concentrates of natural vitamin K containing a powdered milk formula for the purpose of preventing hemorrhagic disease are expensive, while synthetic vitamin K produced for pharmaceutical purposes have not been yet recognized as food additives. For these reasons, addition of vitamin K concentrates to foods is impossible.

In the vitamin K group, only vitamin $K_1$ and $K_2$ naturally occur. Vitamin $K_1$ is abundantly contained in foods, particularly in green vegetables, vegetable oils, seaweeds and so on. For example, seaweeds, layers and tea leaves contain several tens ppm, while soybean oil, spinach and broccoli contain several ppm. Alternatively, vitamin $K_1$ may be synthesized by the condensation of 2-methyl-1,4-naphthoquinone and phythyl acetate. As vitamin $K_2$ compounds, there are known various homologues including menaquinone-1 to -14 (MK-1 to -14) depending on the length of the side chains. Among these, particularly menaquinone-7 (hereinafter, simply referred to as "MK-7") is a representative vitamin $K_2$ substance. MK-7 can be primarily synthesized by *Bacillus natto*, but its isolation is very difficult, because the vitamin $K_2$ content in natto is as small as several to dozen ppm and the half-life of the vitamin $K_2$ is short. The preparation of lipid with high MK-7 content is described probably only in Japanese Unexamined Patent Application Publication No. 8-73396.

For these reasons, production of vitamin $K_2$ in a large amount has been attempted using microorganisms such as *Bacillus natto*. For the production of natural vitamin $K_2$, many studies are known. For example, the following methods are mentioned: a method for collecting vitamin $K_2$ from a culture of a microorganism belonging to the genus Flavobacterium (Japanese Examined Patent Application Publication Nos. 7-28748 and 7-51070); a method for producing vitamin K by inoculating *Bacillus natto* into soybean broth, bean curd refuse or the like supplemented with glycerol to cause fermentation (Japanese Unexamined Patent Application Publication No. 10-295393); and a method for producing vitamin K through fermentation with *Bacillus natto* under conditions of specific culture temperature and time (Japanese Unexamined Patent Application Publication Nos. 8-9916 and 8-19378). In addition to these methods, a method has been proposed in which a fermentation product is extracted with an organic solvent such as an alcohol, an ether, an ester or a ketone to thereby prepare a concentrated lipid which is rich in natural vitamin $K_2$, particularly natural MK-7 (Japanese Unexamined Patent Application Publication No. 8-73396).

However, in the method using a vitamin K-producing bacterium such as Flavobacterium disclosed in Japanese Examined Patent Application Publication Nos. 7-28748 and 7-51070, there is such a problem that a culture or culture broth of Flavobacterium cannot be used in itself as a food additive or a food product, because the safety of Flavobacterium as a food is not yet demonstrated. In the method employing the culture of *Bacillus natto* in soybean broth, bean curd refuse or the like supplemented with glycerol as disclosed in Japanese Unexamined Patent Application Publication No. 10-295393, although a culture with relatively high vitamin K content of up to 40 mg/liter of culture medium can be certainly produced, about 3 to 10% by weight of glycerol may be contaminated in the culture medium and, therefore, glycerol would inevitably remain in the culture. Accordingly, there is such a problem that, although the raw materials of the culture medium (e.g., soybean broth, bean curd refuse) and *Bacillus natto* before cultivation can be used for food, the culture or culture broth given after the cultivation cannot be used in itself as a food additive or for food due to the presence of glycerol therein. In the methods employing the fermentation with *Bacillus natto* under conditions of specific culture temperature and time as disclosed in Japanese Unexamined Patent Application Publication Nos. 8-9916 and 8-19378, a culture with very high vitamin K content of up to about 53 mg/kg soybean and up to about 117 mg/liter culture can be produced, respectively. However, particularly in the method of Japanese Unexamined Patent Application Publication No. 8-9916, the resulting culture is not suitable for a food material because of the smell of ammonia, as described in its specification. In the method disclosed in Japanese Unexamined Patent Application Publication No. 8-19378, although a culture with a high vitamin K content can be produced, most of the produced vitamin K substances are not water-soluble but fat-soluble and, therefore, the use of the vitamin K substances is markedly limited.

The lipid with a high natural menaquinone-7 content prepared by extraction of the fermentation product of *Bacillus natto* with an organic solvent, as disclosed in Japanese Unexamined Patent Application Publication No. 8-73396 is disadvantageous. This is because, although the lipid with high natural menaquinone-7 content can be produced from a raw material (e.g., soybean) applicable for food, the organic solvent should be removed from the lipid completely upon use in a food or as a food, which requires additional facility or time for the removal. Moreover, as mentioned above, the resulting lipid containing menaquinone-7 is fat-soluble as apparent from its name and, therefore, may be limited in use.

As mentioned above, there have been reported the methods for producing vitamin K or menaquinone-7 from natto or a fermentation product of a by-product of the production process for natto (e.g., refuse, broth) with a microorganism (e.g., *Bacillus natto*). However, little report has been found concerning a microorganisms itself which can produce vitamin K or a derivative thereof applicable to food in a high yield.

Accordingly, the object of the present invention is to provide a microorganism capable of producing vitamin K or a derivative thereof with good efficiency.

Disclosure of Invention

The object of the present invention can be achieved by using Yunnan strain SL-001 (FERM BP-6713) which belongs to *Bacillus subtilis*.

BEST MODE FOR CARRYING OUT THE INVENTION

Yunnan strain SL-001 according to the present invention is a new microorganism which belongs to the genus Bacillus, more specifically *Bacillus subtilis*, and is capable of producing vitamin K or a derivative thereof in a high yield.

Hereinbelow, the present invention will be described more detail.

Natto (a product manufactured and sold in Kunming, Yunnan Province, China), which is manufactured using a loquat leaf as a container and by fermenting and aging soybeans in the container was used, and a single strain was isolated therefrom in the following manner in accordance with the dilution separation method as described in the Natto Test Method (pp. 65–66, pub. by Kabushiki Kaisha Korin, ed. by Natto Shiken-ho Kenkyukai, 1990) (in Japanese). The natto was diluted with sterile water, the dilution was cultured on a normal agar medium (10 ml) at 30° C. for 48 hours, formed colonies were inoculated on an inoculating loop after the cultivation for predetermined time, and the procedure was repeated, thereby isolating the desired single strain.

The mycological characteristics of the isolated strain are shown below.
(a) Morphological Characteristics
1) Shape and size of cell: Bacillus, which has a rod-like shape with round edges with a size of 1 $\mu$m (wide)×3–4 $\mu$m (length) when the cells after cultured at 30° C. for 24 hours in a meat broth were directly observed with a microscope.
2) Polymorphology of cell: No polymorphism.
3) Motility: Motile.
More specifically, the presence of motility of the cells was concluded based on both the fact that, when the cells were stab-inoculated on a semisolid medium (a solid medium produced by solidifying a broth medium containing 0.3% of agar into a thick layer) at a depth of ⅔ of the medium and cultured at 35° C., the cell growth was spread over the entire of the medium and the direct observation of the cells with a microscopy.
4) Formation of spores: positive (Thermostable spores were formed)

Each spore has a size of about 1 $\mu$m in diameter. Oval spores were formed at the center portion of the cell. No sporangium was formed.

In item 4) above, briefly, the confirmation of spores was made by staining spores by Moeller method (moellar, H., 1891, Ueber eine neue Methode der Sporenfarbung., Zentbl., Baket. Parasitkde Abt. I, 10, 273). More specifically, cells fixed with fire were stained with a carbol-fuchsin solution, washed with water, decolorized with ethanol, post-stained with Loffler methylene blue solution and then washed with water. As a result, cells were stained in blue, while spores were stained in red. Cells in culture were heated at 80° C. for 10 min, and whether the spores were thermostable or not was determined based on the survival of the cells. As a result, it was found that the spores were thermostable.

(b) Cultural Characteristics

1) Meat broth agar plate culture (30° C., 48 hours): There were formed circular white colonies with wrinkled surface which seems to be dry and with a size of about 2 mm in diameter when cultured at 30° C. for 48 hours.
2) Meat broth liquid culture (30° C.): When a loopful of cells was inoculated into the medium (10 ml) and cultured for 36 hours, a whitish suspension was obtained, the absorbance ($OD_{660}$) of the culture being 0.85.
3) Meat broth gelatin stab culture: +

Cells were inoculated into a gelatin-added agar medium and cultured. After Frazier reagent (Frazier, W. C., 1926, A method for the detection of changes in gelatin due to bacteria., J. Infect. Dis., 37, 302), whether a clear, transparent zone was formed around the cell growth area was observed. The formation of a transparent zone was defined as "positive (+)".

(c) Physiological Characteristics

1) Gram stain: +
2) Nitrate reduction: −
3) VP test: +
4) Productivity of indol: −
5) Productivity of hydrogen sulfide: −
6) Utilization of citrate: −
7) Urease: −
8) Oxidase: +
9) Behavior toward oxygen: aerobic
10) Arginine hydrolysis (arginine dihydrolase activity): −
11) Lysin decarboxylation reaction (lysin decarboxylase activity): −
12) Ornithine decarboxylation reaction (ornithine decarboxylase activity): −
13) Tryptophan deamination reaction: −
14) ONPG test (β-galactosidase activity): −
15) Biotin requirement: −
16) Production of adhesive materials: +

The methods for determination of some of the above-mentioned physiological characteristics are briefly described below.

1) Gram Stain

Gram stain was determined by a modified Hucker method. More specifically, cells fixed with fire were stained with Hucker crystal violet solution, iodinated, decolorized, and then post-stained with Pfeiffer fuchsin solution. As a result, the cells were stained in purple. In this method, a gram positive cell is stained in purple, while a gram negative cell is stained in red.

2) Nitrate Reduction

Cell were inoculated into a nitrate broth medium and cultured. The culture was added with 0.8% sulfanilic acid solution (in 5N acetate solution) and 0.5% α-naphthylamine solution (in 5N acetate solution). A sample that develops red or reddish brown color was defined as "positive".

3) VP Test (Production of Acetoin)

A cell that develops pink to red color in Voges-Proskauer test was defined as "positive". More specifically, cells were inoculated into MR-VP broth medium and cultured at 30° C. for 24 hours. Thereafter, 6% α-naphthol solution (in ethanol) and 40% sodium hydroxide solution were added to the culture and vigorously stirred, followed by allowing to stand. If the culture was color-changed from pink to red, then the cell was determined "positive" (Eddy, B. P., 1961, The Voges-Proskauer reaction and its significance: a review, J. Appl. Bact., 24, 27).

4) Productivity of Indol

Cells were inoculated into aqueous peptone solution prepared for indol test purpose, and then allowed to stand at 35° C. for 10–15 min. Kovacs' reagent was added to the culture. If the culture was developed red color, then the cells were determined "positive" (Kovacs, N., 1928, Eine vereinfachte Methode zum Nachweis der Indolbildung durch Bakterien, Z. ImmunForsch. exp. Ther., 55, 311).

5) Productivity of Hydrogen Sulfide

Cells were inoculated into brucella broth. A lead acetate paper was inserted between the cap and the test tube so that the paper was lopped in the test tube without contacting with the medium. After cultivation, if the end of the paper was color-changed into brown or black, then the cells were determined "positive" (ZoBell, C. E., & Feltham, C. B., 1934, A comparison of lead, bismuth, and iron as detectors of hydrogen sulphide produced by bacteria, J. Bact., 28, 169).

6) Utilization of Citrate

Cells were inoculated into Simmons's citrate agar medium, and then cultured at 35° C. for 4 days. If evident cell growth was observed in the culture and the culture was color-changed into blue, then the cells were determined "positive".

7) Urease cells were richly inoculated into Christensen's urea agar medium and cultured at 35° C. overnight. If the entire medium was color-changed into red, then the cells were determined "positive" (Christensen, W. B., 1946, Urea decomposition as a means of differentiating Proteus and paracolon cultures from each other and from Salmonella and Shigella, J. Bact., 52, 461).

8) Oxidase

Kovacs' reagent was added dropwide to a mass of cells. If the cells were color-changed into dark purple, then the cells was determined "positive" (Kovacs, N., Identification of *Pseudomonas pyocyanea* by the oxidase reaction, Nature, 178, 703, 1956).

9) Behavior Toward Oxygen cells were separately inoculated into two pieces of plate media. One medium was cultured under aerobic conditions, while the other was cultured under anaerobic conditions. For the anaerobic cultivation, gas pack pouch (BBL) was used. If the cells were grown only on the aerobically cultured plate, then the cells were determined "positive".

10-12) Arginine Hydrolysis (Arginine Dihydrolase Activity), Lysin Decarboxylation Reaction (Lysin Decarboxylase Activity) and Ornithine Decarboxylation Reaction (Ornithine Decarboxylase Activity)

Moeller decarboxylase medium was supplemented with each of arginine, lysin and ornithine (all in the form hydrochloride) (1%) and sterilized under high pressure. Cells were inoculated into the medium and steril liquid paraffin was overlaid thereon. If the culture was color-changed into purple, then the cells were determined "positive".

13) Tryptophan Deamination Reaction

Cells were richly inoculated into triptophan agar medium and cultured at 35° C. for 24 hours. Upon addition of 3.4% cupric chloride solution along the slant of the medium, if the area of the slant which contacted with the reagent was color-changed into reddish brown, then the cells were determined "positive".

14) ONPG Test (β-galactosidase Activity)

In ONPG (0-nitrophenyl-β-D-galactopyranoside) test, cells which were color-changed into yellow were determined "positive". That is, cells were inoculated into ONPG broth medium and cultured at 35° C. for 24 hours. If the culture was color-change into yellow, then the cells were determined "positive".

15) Biotin Requirement

A synthetic medium which was developed by Setsuko Kida et al. (Setsuko Kida, Wataru Hashimoto and Shiro Teramoto, Hakko Kogaku Zasshi, in "Nutritional study on natto and *Bacillus natto*" 34, 542, 1956) (in Japanese) was used. Cells were inoculated into the synthetic medium with or without biotin and cultured at 35° C. for 6 days. If the culture became cloudy due to the growth of the cells, then the cells were determined "positive".

16) Production of Adhesive Materials

Cells were inoculated into a plate medium prepared for the purpose of production of adhesive materials (Yotako Muramatsu et al, Abstracts of 1995 National Meeting of Japan Society for Bioscience, Biotechnology and Agrochemistry, p.315, 1995) (in Japanese) and cultured. If production of any adhesive material was observed on the formed colonies, the cells were determined "positive".

(d) Formation of Acids from Sugars

The presence or absence of the formation of any acid from different sugars by the cells are shown below.

For examination of the formation of acids from the below-listed sugars (carbohydrates), cells were inoculated into a sugar-added ammonium agar medium supplemented with each of the carbohydrates to a final concentration of 1%, and cultured at 35° C. for 4 days. If the culture was color-changed into yellow, then the cells were determined "positive".

1) Glycerol: ±
2) L-Arabinose: −
3) Ribose: −
4) D-Glucose: +
5) D-Fructose: ±
6) D-Mannose: +
7) Inositol: −
8) D-Mannitol: −
9) D-Sorbitol: −
10) α-Methyl-D-glycoside: ±
11) Esculin: +
12) Maltose: −
13) Saccharose: +
14) Trehalose: +
15) Inulin: +
16) Glycogen: +

The strain was classified and identified with reference to Bergey's Manual of Systematic Bacteriology (8th) or the like. As a result, it was found that the strain was close to *Bacillus subtilis*.

With respect to the characteristics of items (a) to (d), the strain isolated from the natto manufactured and sold in Kunming, Yunnan Province, China described above was compared with Maburg (a typical reference strain of *Bacillus subtilis*) and commercial *Bacillus natto* strains, Miyagino strain (Yugen Kaisha Miyagino Natto Seizoujo, Sendai), Yayoi strain (Suzuyo Kogyo Co., Ltd., Tokyo), Takahashi strain (Takahashi Yuzo Kenkyujo, Yamagata) and Naruse strain (Kabushiki Kaisha Naruse Hakko Kagaku Kenkyujo, Tokyo). The results are shown in Tables 1 to 3.

TABLE 1

| Characteristics | Marburg | Commercial *Bacillus natto* strains | | | | Isolated strain |
| --- | --- | --- | --- | --- | --- | --- |
| | | Miyagino | Yayoi | Takahashi | Naruse | |
| Morphology | bacillus | bacillus | bacillus | bacillus | bacillus | bacillus |
| Motility | + | + | + | + | + | + |
| Formation of spore | + | + | + | + | + | + |
| Liquifiability of gelatin | + | + | + | + | + | + |
| Gram stain | positive | positive | positive | positive | positive | positive |
| Nitrate reduction | + | − | − | − | − | − |
| VP test | + | + | + | + | + | + |
| Productibity of indol | − | − | − | − | − | − |
| Productivity of hydrogen sulfide | − | − | − | − | − | − |
| Utilization of citrate | + | ± | ± | ± | ± | − |
| Urease | − | − | − | − | − | − |
| Oxidase | | + | + | + | + | + |
| Behavior toward oxygen | aerobic | aerobic | aerobic | aerobic | aerobic | aerobic |
| Arginine hydrolysis | − | − | − | − | − | − |

TABLE 2

| Characteristics | Marburg | Commercial *Bacillus natto* strains | | | | Isolated strain |
| --- | --- | --- | --- | --- | --- | --- |
| | | Miyagino | Yayoi | Takahashi | Naruse | |
| Lysin decarboxylation reaction | − | − | − | − | − | − |
| Ornithine decarboxylation reaction | − | − | − | − | − | − |
| Tryptophan deamination reaction | − | − | − | − | − | − |
| ONPG test | + | + | + | + | + | − |
| Biotin requirement | − | + | + | + | + | − |
| Production of adhesive materials | − | + | + | + | + | + |
| Formation of acids from sugars | | | | | | |
| Glycerol | + | + | + | + | + | ± |
| L-Arabinose | + | + | + | + | + | − |
| Ribose | + | + | + | + | + | − |
| D-Glucose | + | + | + | + | + | + |
| D-Fructose | + | + | + | + | + | ± |

TABLE 2-continued

| Characteristics | Marburg | Commercial *Bacillus natto* strains | | | | Isolated strain |
|---|---|---|---|---|---|---|
| | | Miyagino | Yayoi | Takahashi | Naruse | |
| D-Mannose | + | + | + | + | + | + |
| Inositol | + | + | + | + | + | − |
| D-Mannitol | + | + | + | + | + | − |

TABLE 3

| Characteristics | Marburg | Commercial *Bacillus natto* strains | | | | Isolated strain |
|---|---|---|---|---|---|---|
| | | Miyagino | Yayoi | Takahashi | Naruse | |
| Lysin decarboxylation reaction | − | − | − | − | − | − |
| Ornithine decarboxylation reaction | − | − | − | − | − | − |
| Tryptophan deamination reaction | − | − | − | − | − | − |
| ONPG test | + | + | + | + | + | − |
| Biotin requirement | − | + | + | + | + | − |
| Production of adhesive materials | − | + | + | + | + | + |
| Formation of acids from sugars | | | | | | |
| Glycerol | + | + | + | + | + | ± |
| L-Arabinose | + | + | + | + | + | − |
| Ribose | + | + | + | + | + | − |
| D-Glucose | + | + | + | + | + | + |
| D-Fructose | + | + | + | + | + | ± |
| D-Mannose | + | + | + | + | + | + |
| Inositol | + | + | + | + | + | − |
| D-Mannitol | + | + | + | + | + | − |

The results in Tables 1 to 3 demonstrate that, with respect to the utilization of citrate, ONPG test (β-galactosidase activity) and biotin requirement, the strain isolated from the natto manufactured and sold in Kunming, Yunnan Province, China showed significant difference compared with other *Bacillus subtilis* strains, particularly commercial *Bacillus subtilis* strains. The results also demonstrate that, with respect to the production of acids from sugars, the strain isolated from the natto manufactured and sold in Kunming, Yunnan Province, China showed significant difference in the production of L-arabinose, ribose, inositol, D-mannitol, D-sorbitol, maltose and glycogen, compared with other *Bacillus subtilis* strains, particularly commercial *Bacillus subtilis* strains.

The DNA pattern was compared between the strain isolated from the natto manufactured and sold in Kunming, Yunnan Province, China and commercial *Bacillus natto* strains, Miyagino strain (Yugen Kaisha Miyagino Natto Seizoujo, Sendai), Yayoi strain (Suzuyo Kogyo Co., Ltd., Tokyo), Takahashi strain (Takahashi Yuzo Kenkyujo, Yamagata) and Naruse strain (Kabushiki Kaisha Naruse Hakko Kagaku Kenkyujo, Tokyo) in accordance with RAPD method [Kazuko Nishimoto, Hiroshi Kawaguchi, Tamami Yokote, Noriaki Kishimoto and Tatsuo Tano, Abstracts of 1999 National Meeting of Japan Society for Bioscience, Biotechnology and Agrochemistry, in "Convenient classification method of *Bacillus natto* strains using RAPD (random amplified polymorphic DNA), p. 75, 1999 (in Japanese); Hiroshi Kawaguchi, Kazuko Nishimoto, Tamami Yokote, Hideki Morishita, Noriaki Kishimoto and Tatsuo Tano, Abstracts of 46th National Meeting of Japan Foods and Science Technology, in "classification of food microorganisms at a strain level using RAPD method", p. 98]. The results are shown in FIG. 1.

Figure 1:
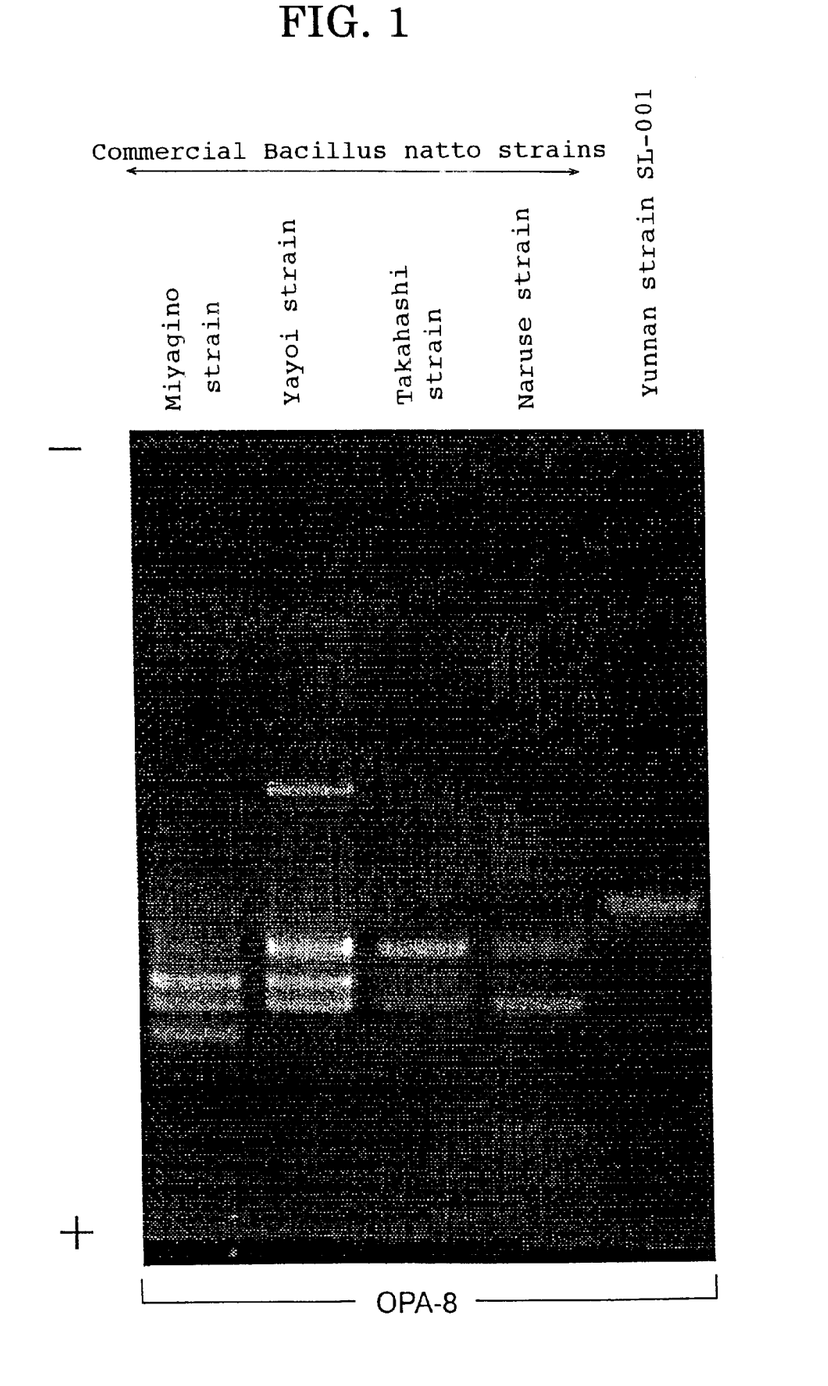
FIG. 1 shows DNA patterns of Yunnan strain SL-001, Miyagino strain, Yayoi strain, Takahashi strain and Naruse strain determined by the RAPD method.

As shown in FIG. 1, the strain isolated from the natto manufactured and sold in Kunming, Yunnan Province, China (Yunnan strain SL-001 in FIG. 1) showed a DNA pattern clearly distinct from other four commercial *Bacillus natto* strains.

In addition to the difference as mentioned above, when the amounts of menaquinone-7 (one of vitamin K substances) and a derivative thereof in cultured cells and a culture medium were determined for each of the strain isolated from the natto manufactured and sold in Kunming, Yunnan Province, China and the various commercial *Bacillus natto* strains, there was a significant difference in the amounts among them, as described in detail in EXAMPLES below.

These results demonstrate that the strain of the present invention has distinct characteristics from known *Bacillus subtilis* strains. Accordingly, this strain is decided to be a new microorganism belonging *Bacillus subtilis* and designated "Yunnan strain SL-001", which has been deposited under the terms of Budapest Treaty at the National Institute of Bioscience and Human-Technology, Agency of Industrial Science and Technology, Japan, (1–3, Higashi 1-chome, Tsukuba-shi, Ibaragi-ken, Japan) on May 7, 1999 under the accession No. FERM BP-6713.

The present inventors have found that, when cells of Yunnan strain SL-001 were collected from a culture by any known method (e.g., filtration and centrifugation), dried by any known method (e.g., freeze-drying, air-drying and heat-drying under vacuo), the dried cells can dissolved in water. Then, the culture was extracted with water and isopropanol separately and analyzed by HPLC, as described in detail in EXAMPLES below. As a result, it was found that both the extracts contained vitamin K (particularly MK-7). This result suggests that the vitamin K (particularly MK-7) produced by Yunnan strain SL-001 of the present invention would undergo some change within the cell so that it was made water-soluble. The vitamin K and menaquinone-7 (MK-7) in the forms imparted with water-solubility are designated "water-soluble vitamin K derivative" (or simply "vitamin K derivative") and "water-soluble menaquinone-7 derivative" (or simply "MK-7 derivative"), respectively. The water-soluble menaquinone-7 derivative showed a single band corresponding to a molecular weight of about 100,000 as determined by SDS-polyacrylamide gel electrophoresis, and also showed a molecular weight not smaller than 100,000 as determined by gel filtration, as also mentioned in detail in Examples below. From these results, in view of the fact that the molecular weight of menaquinone-7 is about 649, it is presumed that any substance (e.g., sugar protein) binds to MK-7 to thereby change the MK-7 in a stable form, forming water-soluble vitamin K derivatives (including vitamin $K_2$ derivative and menaquinone-7 derivative; this explanation is omitted hereinafter) in the cells. However, off course, it will be appreciated that this presumption is not intended to limit the concept of the present invention.

In the present invention, the cultivation of Yunnan strain SL-001 cells can be performed in the similar medium under the similar culture conditions to those employed for the conventional cultivation-of *Bacillus subtilis*. For example, the medium usable for the cultivation of the present invention is not particularly limited and may be any medium made of components known to those skilled in the art. The medium may be a medium prepared by mixing various culture components appropriately, commercially available medium per se, or a commercially available medium added with the aforementioned known components as supplementary components. The medium may be of solid or liquid and suitably selected depending on the intended use. In addition, as long as the medium contains a carbon source, an appropriate amount of nitrogen source, an inorganic salt and any other nutrient source assimilatable by the microorganism used, the medium may be of synthetic or natural.

The carbon source usable for the cultivation of Yunnan strain SL-001 of the present invention is not particularly limited as long as it can be assimilated by the strain. Specific examples of the carbon source include carbohydrates, such as starch or its composite fraction, roasted dextrin, processed starch, starch derivative, physically processed starch, α-starch, soluble starch, amylose, amylopectin, maltooligosaccharaide, cyclodextrin, pluran, corn starch, potato starch, sweet potato starch and dextrin, glycerin, galactose, lactose, malt extract, glucose, fructose, mannose, R-methyl-D-glycoside, esculin, saccharose, trehalose, inulin and glycogen. Among these carbon sources, saccharose, mannose, esculin, glucose, starch, trehalose, inulin and glycogen are preferably used, from the viewpoint of growth of Yunnan strain SL-001. These carbon source can be used singly or in combination of two or more of them.

The nitrogen source usable for the cultivation of Yunnan strain SL-001 of the present invention is also not particularly limited as long as it can be assimilated by the strain. Specific examples include meat extract, malt extract, peptone, soybean-derived polypeptone (e.g., Polypeptone-S), yeast extract, "ajieki" (a hydrolysate of soybean protein), soybean powder, milk casein, various amino acids (e.g., casamino acids, glutamic acid, arginine, asparatine and proline) and organic nitrogen compounds such as corn steep liquor, as well as ammonium salts such as ammonia, ammonium carbonate, ammonium nitrate, ammonium sulfate and ammonium chloride and sodium salts such as sodium nitrate and sodium sulfate, and inorganic nitrogen compounds such as urea and uric acid. Among these nitrogen sources, soybean-derived polypeptone (e.g., Polypeptone-S) and soybean powder are preferably used, from the viewpoint of growth of Yunnan strain SL-001. These nitrogen sources may also be used singly or in combination of two or more of them.

The inorganic salts usable for the cultivation of Yunnan strain SL-001 of the present invention is also not particularly limited as long as the strain can grow satisfactory on the medium. Specifically, one, two or more members selected from phosphates, hydrochlorides, sulfates and acetates of magnesium, manganese, calcium, sodium, potassium, copper, iron and zinc may be used.

A vitamin may also be contained in the medium for the cultivation of Yunnan strain SL-001 of the present invention. The vitamin is also not particularly limited as long as Yunnan strain SL-001 can grow satisfactory on the medium. Specific examples of the vitamin include thiamin, riboflavin, vitamin $B_6$ compounds, calcium pantothenate, nicotinic acid amide, p-aminobenzoic acid and folic acid.

When a commercially available medium is used for the cultivation of Yunnan strain SL-001 of the present invention, the medium includes, for example, nutrient broth (dry broth) (a product of Nissui Pharmaceutical Co., Ltd. or Nippon Seiyaku Kabushiki Kaisha), Polypepton-S (a product of Wako Pure Chemical industries, Ltd.).

In the present invention, the medium used for the cultivation of Yunnan strain SL-001 may be a material which can be fermented by *Bacillus natto*, such as okara (an unextracted residue of soybeans), soybeans, soybean broth which is a by-product of the production of miso (fermented soy paste) or natto (slippery fermented soybeans), tofu (bean curd) refuse which is a by-product of the production of tofu or aburage (fried bean curd), soybean refuse which is a by-product of the production of oils from soybeans and seed coat of soybeans which is a by-product of the production of miso. If necessary, the aforementioned carbon source, nitrogen source or inorganic salt may be appropriately added to the material.

In the present invention, the cultivation of Yunnan strain SL-001 may be performed in the same manner as in conventional methods. The conditions for cultivation may be suitably selected depending on the composition of the culture medium and the method of cultivation employed, and is not particularly limited as long as the strain can grow satisfactorily. The temperature of cultivation is generally within the range from 20 to 45° C., preferably from 37 to 42° C. The pH of the culture medium suitable for the cultivation is generally within the range from 6.0 to 9.5, preferably from 7.0 to 8.5.

The culture and culture broth of Yunnan strain SL-001 of the present invention thus prepared are highly safe, because the strain utilizes foods as sources. Hence, the culture or culture broth of Yunnan strain SL-011 of the present invention in itself can be used as a food additive or food product.

Yunnan strain SL-001 of the present invention is capable of producing vitamin K or a derivative thereof with good efficiency. The method for isolation and purification of the vitamin K or derivative thereof from Yunnan strain SL-001 may vary depending on the conditions of cultivation and so on, as described below in detail. For example, in the case where the desired vitamin K or the derivative thereof is accumulated in cells in culture, the following method may be employed: cells are cultured under the aforementioned conditions, collected by filtration, centrifugation or the like, subjected to physical means (e.g., freeze-thawing, ultrasonication, pressure-treatment, treatment under osmotic difference, grinding, etc.) or chemical means (e.g., treatment with an enzyme capable of lysis of cell walls, such as lysozyme; or treatment by contacting with a surfactant) singly or in combination thereof, thereby disrupting the cells, and then purifying the desired vitamin K or derivative thereof from the disrupted cells by any known method (e.g., fractional crystallization, fractional precipitation, ion exchange chromatography, solvent extraction, etc.) singly or in combination thereof.

The cells in culture may be subjected to Soxhlet extraction to collect the vitamin K or derivative thereof. Specifically, the cells cultured as mentioned above are subjected to Soxhlet extraction with an organic solvent (e.g., hexane, diethyl ether, acetone, ethanol, isopropanol) at a boiling point of the organic solvent employed using Soxhlet extractor, thereby producing a fat-soluble fraction. The fraction is then extracted with an organic solvent (e.g., hexane, diethyl ether, acetone, ethanol, isopropanol) at 30–100° C. for 0.1–20 hours. The resulting extract is diluted with an organic solvent as mentioned above to a predetermined total volume. An aliquot of the diluted extract is mixed with water and isopropanol, and then further mixed with an organic solvent as mentioned above using a touch mixer or other means. The resulting mixed solution is centrifuged, and the supernatant is evaporated to dryness. The residue is dissolved in ethanol, thereby yielding vitamin K or derivative thereof.

In the present invention, when the vitamin K derivative produced by Yunnan strain SL-001 is water-soluble, the following procedure may be employed to collect the desired vitamin K derivative. Briefly, a culture broth or culture supernatant of the cells of Yunnan strain SL-001 cultured as mentioned above is treated so that the pH is lowered, preferably to 1–3 to thereby produce a precipitate. The precipitate is fractionated by centrifugation or the like to yield the water-soluble vitamin K derivative.

The vitamin K or derivative thereof from the culture or culture broth of Yunnan strain SL-001 of the present invention thus prepared is also highly safe, because Yunan strain SL-001 utilizes foods as sources and therefore its culture or culture broth is safe. Therefore, the culture or culture broth of Yunnan strain SL-011 of the present invention in itself can be used as a food additive or food product.

Hereinbelow, the present invention will be described more in detail by way of examples.

EXAMPLE 1

Okara (Asahimatsu Foods Co., Ltd., Iida-shi) (10 g; wet weight) was placed in a petri dish and autoclaved at 120° C. for about 10 min. (sterilization in an autoclave).

On the other hand, a loopful of each of seven kinds of *Bacillus natto* strains, comprising four kinds of *Bacillus natto* strains (Miyagino strain, Asahi strain, Naruse strain and Takahashi strain) which have been used in commercial natto products and maintained in an individual slants, two kinds of *Bacillus natto* strains (Nitto strain and Meguro strain) which have been used as pharmaceuticals and Yunnas strain SL-001 (FERM BP-6713), was suspended in sterile water (9.5 ml) to prepare a cell suspension. The commercial *Bacillus natto* strains are as follows. Hereinafter, only a strain name is shown for each of the *Bacillus natto* strains used.

Commercially Available *Bacillus natto* Strains

Miyagino strain (Yugen Kaisha Miyagino Natto Seizoujo, Sendai)
Nitto strain (Nitto Pharmaceutical Industries, Ltd., Kyoto)
Meguro strain (Kabushiki Kaisha Meguro Kenkyujo, Osaka)
Asahi strain (Kabushiki Kaisha Asahi Kogyo, Tokyo)
Naruse strain (Kabushiki Kaisha Naruse Hakko Kagaku Kenkyujo, Tokyo)
Takahashi strain (Takahashi Yuzo Kenkyujo, Yamagata)

Each of the cell suspensions prepared above (0.5 ml) was inoculated into the okara autoclaved in above and incubated at 37° C. for 4 days.

Figure 2:
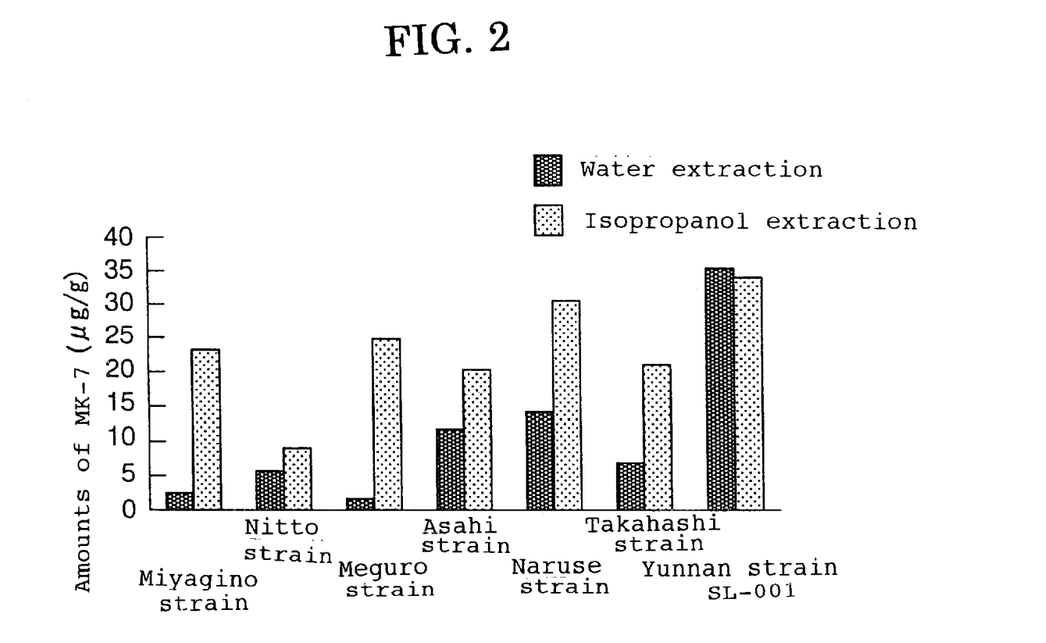
FIG. 2 is a graph showing the amounts of MK-7 in water-extracts and isopropanol-extracts of cultures of different *Bacillus natto* strains four days after the cultivation in Example 1.

The okara-culture of each *Bacillus natto* strain was added with 4-volumes of distilled water or isopropanol. The mixed solution was centrifuged at 20° C. at 3,000 rpm for 10 min., and the resulting supernatant (0.5 ml) was used as an extraction sample. For each of the extraction samples prepared with distilled water as the extraction solvent, distilled water (0.5 ml) and isopropanol (1.5 ml) were mixed therewith. For each of the extraction samples prepared with isopropanol as the extraction solvent, distilled water (1.0 ml) and isopropanol (1.0 ml) were mixed therewith. Subsequently, the resulting mixed solution was added with hexane (5.0 ml), stirred and then centrifuged at 20° C. at 3,000 rpm for 10 min. The hexane layer (4.0 ml) was concentrated and dried with an evaporator, and the resulting residue was dissolved in ethanol (100 $\mu$l). The samples prepared using either distilled water or isopropanol as an extraction solvent were used as the water-extracted samples and isopropanol-extracted samples, respectively. The water-extracted samples and isopropanol-extracted samples thus prepared were used to determine the MK-7 content under the HPLC conditions shown below. The results are shown in FIG. 2. As shown in FIG. 2, Yunnan strain SL-001 of the present invention had higher MK-7 content both in the water-extracted samples and the isopropanol-extracted sample and showed a significant difference in MK-7 content particularly in the water-extracted sample, as compared with other commercial *Bacillus natto* strains.

In the present example, the determination of MK-7 content by high performance liquid chromatography (HPLC) utilizes the fact that vitamin K is reduced with platinum-alumina catalyst into a fluorescent hydroquinone form, and specifically performed under the following conditions.

Apparatus:
    pump: PU-980 (Nippon Bunko)
    injector: 7125 (Nippon Bunko)
    column oven: CO-965 (Nippon Bunko)
    detector: Fluorescence detector 821-FP (Nippon Bunko)
    date processing device: C-R5A (Shimadzu Corporation)
Conditions:
    column: ODS-II column (4.6×250 mm) (Shimadzu Corporation)
    reduction column: platinum-alumina catalyst column (Wako Pure Chemical Industries, Ltd.; primary grade platinum-alumina, packing about 0.2 g of Pt=5%; 4.0$\phi$×10 mm)
    mobile phase: 97% ethanol (flow rate: 0.7 ml/min)
    temperature for separation/reduction: 40° C.
    measuring wavelength: excitation 320 nm fluorescence 430 nm
    amount of injection: 10 $\mu$l In accordance with this determination method, calibration curves for MK-7, menaquinone-7 and vitamin $K_1$ were established, respectively. As a result, it was found that the amount of MK-7 was able to determination within the range of 0.05 to 50 ng in accordance with the equation [$-0.89661+1.6993 \times 10^{-6} \times$(area of HPLC corresponding to vitamin K ($\mu$V, sec))], and the amounts of menaquinone-4 and vitamin $K^1$ were able to determination within the range of 0.01 to 10 ng in accordance with the equation [$-0.58657+4.8030 \times 10^{-9} \times$(area of HPLC corresponding to vitamin K ($\mu$V, sec))] and the equation [$-0.44381+4.0626 \times 10^{-7} \times$(area of HPLC corresponding to vitamin K ($\mu$V, sec))], respectively.

The standard substance for MK-7 for the establishment of the calibration curve was prepared as follows. Natto (600 g) was added with 75% isopropanol (1 liter) and n-hexane (1 liter), gently stirred for 1 hour and then allowed to stand. Among the separated two layers, the upper layer was removed, dried over sodium sulfate anhydride and evaporated to dryness, thereby yielding an extract (about 20 g). The extract was mixed with n-hexane (10 ml), passed through chromatography silica gel (400 ml) to adsorb the extract onto the silica gel, and then eluted and fractionated with n-hexane/toluene (1:1) (2 liters). A fraction containing MK-7 was evaporated to dryness under vacuo. The resulting silica gel concentrate was dissolved in n-hexane (5 ml), fractionated again with a silica gel column in the same manner as above, and evaporated to dryness under vacuo, thereby yielding a product (about 350 mg). An aliquot (50 mg) of the product was dissolved in a small volume of acetone, passed through chromatography ODS-silica gel (60 ml) filled with acetonitrile/methanol (1:1), and then developed with acetonitrile/methanol (1:1). The elute was monitored by HPLC to collect a fraction in which a substance suspected to be MK-7 alone was eluted. The fraction was evaporated to dryness under vacuo. For the resulting substance, an IR spectrum and a mass spectrum were obtained to confirm that the substance was MK-7. The purity of the substance was revealed to be 99.8%. The standard substances for forphylloquinone (vitamin $K_1$) and menaquinone-4 (MK-4) used were of special grade (Sigma). The measurement was performed on three extracts for each sample and these values are averaged.

EXAMPLE 2

A water-extracted sample for Yunnan strain SL-001 was prepared in the same manner as in EXAMPLE 1, and examined on the thrombolytic property in accordance with the fibrin plating method. Briefly, the water-extracted sample (30 µl) was placed on artificial thrombus prepared in a petri dish (standard fibrin plate) (H. Sumi et al., Experientia, 43:1110–111, 1987), and incubated at 37° C. for 1 hour. As a result, thrombolysis was observed. This result demonstrates that the water-extracted sample of Yunnan strain SL-001 exhibited thrombolytic activity by the action of Natto kinase (NK).

EXAMPLE 3

A water-extracted sample of Yunnan strain SL-001 was prepared in the same manner as in EXAMPLE 1, and evaluated on the ability to decompose or break down a substrate for plasmin in accordance with the synthetic substrate decomposition method. Specifically, the water-extracted sample (10 µl) and $5 \times 10^{-3}$ M S-2251 (a substrate for plasmin; H-D-Val-Leu-Lys-pNA) (20 µl) were added with 0.1 M Tris buffer (pH 7.4) (170 µl), and then incubated at 37° C. for 1 hour. The solution showed an absorbance at 405 nm ($A_{405}$) of 0.168 and the bread down of S-2251 was observed. These results demonstrate that the water-extracted sample of Yunnan strain SL-001 has thrombolitic activity by the action of Natto kinase (NK).

EXAMPLE 4

Okara (Asahimatsu Foods Co., Ltd., Iida-shi) (10 g; wet weight) was placed in a petri dish and autoclaved at 120° C. for about 10 min. (sterilization in an autoclave).

On the other hand, a loopful of each of Miyagino strain (a commercially available Bacillus natto strain) and Yunnan strain SL-001 (FERM BP-6713), both which had been maintained on a slant, was suspended in sterile water (9.5 ml). The cell suspension (0.5 ml) was inoculated into the okara which had been autoclaved above and incubated at 37° C. for 10 days.

During the cultivation, the okara culture with Bacillus natto was sampled with passage of time (on day 1, 2, 4, 6, 8 and 10). An isopropanol-extracted sample was prepared from the culture in the same manner as in EXAMPLE 1, and the MK-7 content of the isopropanol-extracted sample was determined in the same manner as in EXAMPLE 1. The results are shown in FIG. 3.

Figure 3:
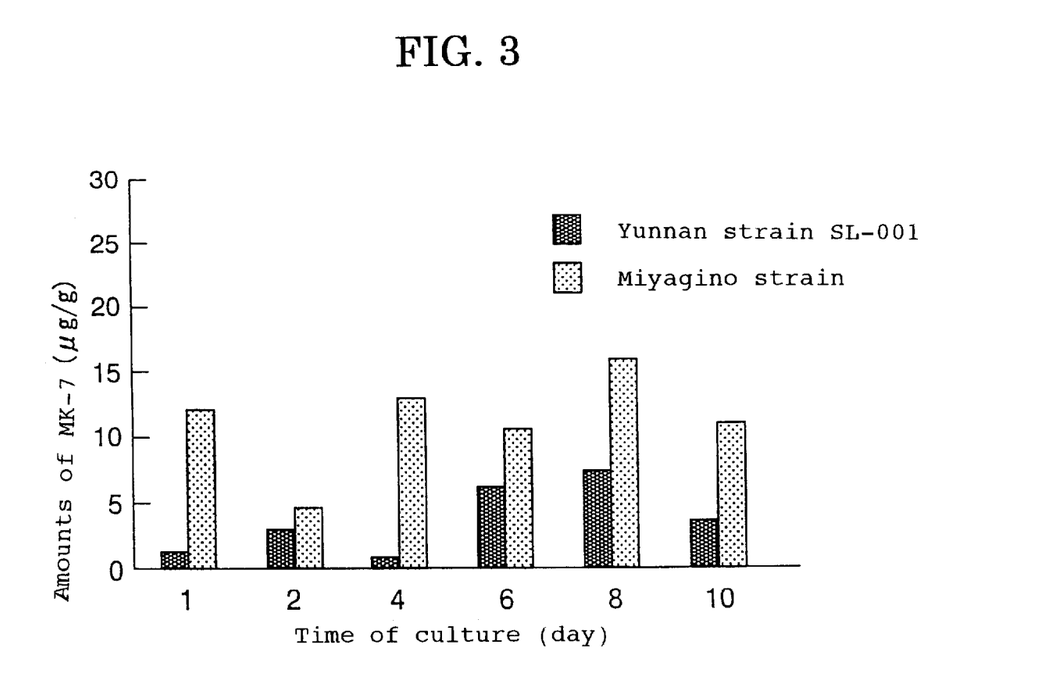
FIG. 3 is a graph showing the amounts of MK-7 in isopropanol-extracts of cultures of Miyagino strain and Yunnan strain SL-001 versus time of cultivation in Example 4.

As shown in FIG. 3, in the culture of Yunnan strain SL-001 of the present invention, significantly higher MK-contents were shown at all of the sampled culture time points and the MK-7 content reached a peak in a shorter time, compared with Miyagino strain (a typical, commercially available Bacillus natto strain). These results demonstrate that Yunnan strain SL-001 of the present invention can produce MK-7 (one of vitamin K substances) rapidly and efficiently and very suitable for the mass production of MK-7.

EXAMPLE 5

Okara (Asahimatsu Foods Co., Ltd., Iida-shi) was frozen and stored at −25° C. and thawed as required before use. The thawed okara was autoclaved at 120° C. for 30 min. and then placed in a ca. 120-ml of polystyrene paper (PSP) container and used as a culture medium for Bacillus natto strains.

On the other hand, each of seven kinds of Bacillus strains, consisting of four kinds of Bacillus natto strains (Takahashi strain, Naruse strain, Miyagino strain and Asahi strain) which have been used in commercial natto products, two kinds of Bacillus natto strains (Nitto strain and Meguro strain) which have been used as pharmaceuticals, and Yunnan strain SL-001, was cultured with shaking (100 rpm) in a culture medium (150 ml) containing 3% nutrient broth (dried broth) (Nissui Pharmaceutical Co., Ltd.) at 37° C. for 3 days, thereby producing pre-cultures of the aforementioned seven kinds of Bacillus natto strains.

The pre-culture of each of the seven kinds of Bacillus natto strains (viral cells: $2 \times 10^8$ cells/ml) (0.5 ml) was added to the okara prepared above (wet weight: 50 g), and allowed to ferment statically at 37° C. On day 4 of the fermentation, the cells of each of the Bacillus natto strains were suspended in water, filtrated through a metal tea strainer and then centrifuged (3,000 rpm×10 min.), thereby producing a culture of each strain. A water-extracted sample was prepared from the culture in the same manner as in EXAMPLE 1, the amount of MK-7 derivative in the sample was determined in accordance with the method described in EXAMPLE 1. The results are shown in FIG. 4.

Figure 4:
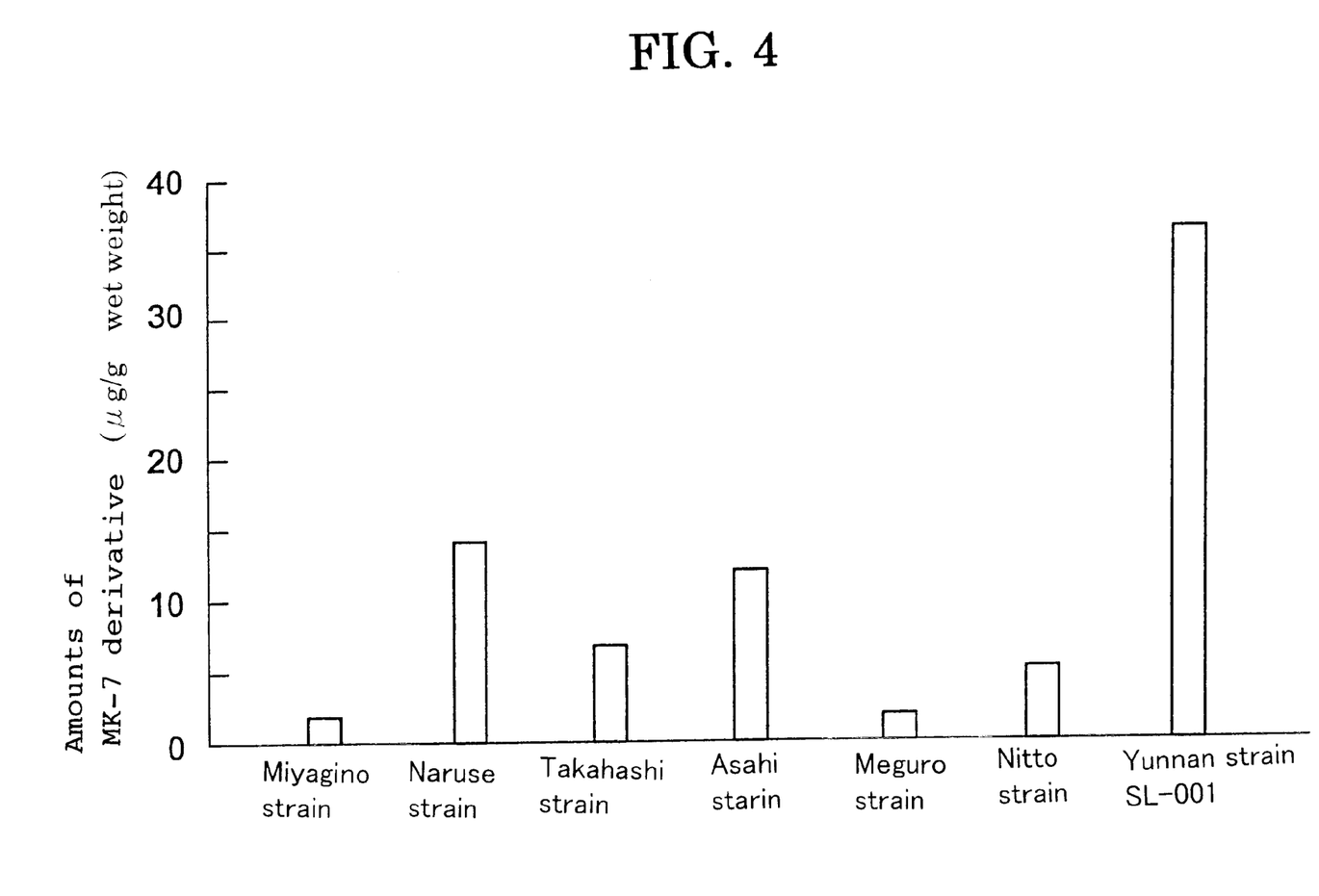
FIG. 4 is a graph showing the amounts of a MK-7 derivative in water-extracts of cultures of different *Bacillus natto* strains four days after the cultivation in Example 5.

As shown in FIG. 4, the yield of the MK-7 derivative in the culture of each Bacillus natto strain after cultivation for 4 days was, in average, 36.6 µg/g okara (wet weight) for Yunnan strain SL-001; 1.9 µg/g okara (wet weight) for Miyagino strain; 14.2 µg/g okara (wet weight) for Naruse strain; 6.8 µg/g okara (wet weight) for Takahashi strain; 11.9 µg/g okara (wet weight) for Asahi strain; 1.9 µg/g okara (wet weight) for Meguro strain; and 5.2 µg/g okara (wet weight) for Nitto strain. As is evident from these results, Yunnan strain SL-001 of the present invention showed a MK-7 yield as high as 36.6 µg/g of okara (wet weight), which is mathematically 2 to 20 times higher than those of other Bacillus natto strains and four times higher than the reported analytical values for natto (6.2 to 8.7 µg/g okara in wet weight) (Michio Yanaguchi ed., Japan Food Ingredient List, Ishiyaku Shuppan, Tokyo, pp. 52–53, 1997 (in Japanese); Toshiyuki Sakano et al., Vitamin, 62: 393–398, 1988; H. Ikeda and Y. Doi, Eur. J. Biochem., 192:219–223, 1990; and Hiro Ikeda, Journal of Domestic Science, 43:643–648, 1992 (in Japanese)).

EXAMPLE 6

Okara provided by Asahimatsu Foods Co., Ltd. (Iida-shi) was frozen and stored at −25° C. and thawed as required before use.

On the other hand, Yunnan strain SL-001 was cultured with shaking (100 rpm) in a culture medium (150 ml) containing 3% nutrient broth (dried broth) (Nissui Pharmaceutical Co., Ltd.) in a 500-ml conical flask at 37° C. for 3 days, thereby producing a pre-culture of the *Bacillus natto* strain.

The thawed okara (1 kg; wet weight) was autoclaved at 120° C. for 30 min. and then placed in a ca. 120-ml of polystyrene paper (PSP) container. The pre-culture of Yunnan strain SL-001 prepared above was added to the container and allowed to ferment at 37° C. for 4 days. Water is added to the fermented okara-natto at a mixing ratio of 5 liters per kg the okara-natto (wet weight). The mixture was stirred at room temperature for 1 hour and then centrifuged (3,000 rpm, 10 min.). The supernatant was added with ion exchange resin (DEAE-Sepharose CL-613) (620 g) and stirred, followed by allowing to stand at room temperature for 30 min. The mixture was packed in a glass column (7.5 cm$\phi$×100 cm), washed with distilled water and 0.05M phosphate buffer (pH 7.0), and then subjected to gradient elution with 0.05M phosphate buffer (pH 7.0) containing 0.1 to 0.8 NaCl. The amount of vitamin K was determined for each fraction by the HPLC method in the same manner as in EXAMPLE 1, and fractions containing vitamin K were concentrated using a membrane filter (Millipore; MW 10,000), dialyzed against distilled water, and then freeze-dried, thereby yielding water-soluble vitamin K derivative as pale yellow powder.

Figure 5:
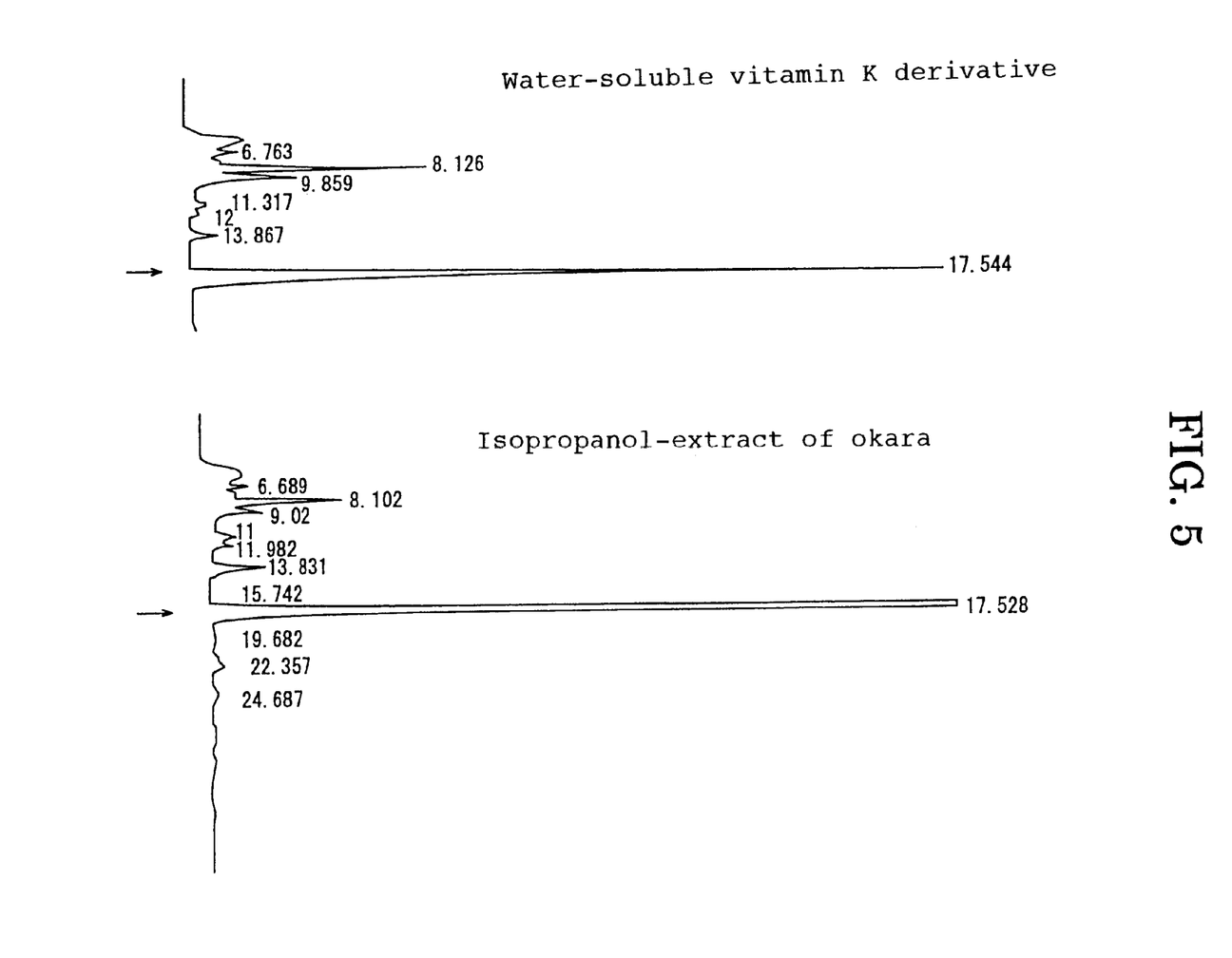
FIG. 5 is a graph showing the results of HPLC analysis of a water-soluble vitamin K derivative and an isopropanol-extract sample of a culture of "okara" (an unextracted residue of soybeans) in Example 6.

The water-soluble vitamin K derivative thus obtained and the extract of the same okara as above with isopropanol were analyzed by HPLC. The results are shown in FIG. 5. In FIG. 5, the retention times for MK-4, vitamin $K_1$ and MK-7 were about 8.2 min., about 11.3 min. and about 17.5 min., respectively, and arrows indicate the retention time for MK-7. As shown in FIG. 8, it was found that 60% or more of the isopropanol extract of the okara was extracted into the water-soluble fraction, are that, among the vitamin K substances, the amounts of vitamin $K_1$ and MK-4 were smaller and MK-7 made up over 95% of the vitamin K content.

The water-soluble vitamin K derivative was analyzed by SDS-polyacrylamide gel electrophoresis. As a result, a single band, although broad, was observed at the position corresponding to MW of about 100,000. This result suggests that the water-soluble vitamin K derivative, together with any other sugar protein, would form a complex with MW of about 100,000. The yield of the water-soluble vitamin K derivative from 1 kg of the natto was about 5.3 g (830 $\mu$g of water-soluble MK-7 derivative per g) as determined by averaging three determination results.

EXAMPLE 7

A culture medium containing 3% of dry broth (Nissui Pharmaceutical Co., Ltd.) (300 ml) was added to each of five 500-ml conical flasks, and autoclaved at 120° C. for 15 min. A loopful of Yunnan strain SL-001 was inoculated to each of the medium and cultured with shaking (100 rpm) at 37° C. After 4 days, the cultures were combined and centrifuged (5,000 rpm×10 min.). The supernatant was divided into three 400 ml-portions and adjusted to pH. 1.02, 2.07 and 3.01, respectively, with dilute hydrochloric acid. Each of the solutions was allowed to stand at room temperature for 3 hours, and the supernatant was centrifuged (5,000 rpm×10 min., 10° C.), thereby separating a white precipitate. The white precipitate was dissolved in a small volume of distilled water and adjusted to pH 7.0 with ammonium bicarbonate powder, followed by freeze-drying. The amounts of the freeze-dried products were 0.52 g, 0.28 g and 0.31 g for the samples which had been adjusted to pH 1.02, 2.07 and 3.01, respectively. This procedure was repeated.

The freeze-dried product (1 g: dry weight) was extracted with hexane (100 ml) in Soxhlet extractor (SIBATA SPC 34, WATER BATH SIBATA WB-6C, filter: ADVANTEC 84, 24×100 mm) at 80° C. for 6 hours. The total volume of the extract was adjusted to 100 ml with hexane. The extract (100 $\mu$l) was mixed with distilled water (1.0 ml) and isopropanol (1.5 ml) and then further mixed with hexane (4.9 ml) with a touch mixer for about 10 sec. The mixed solution was centrifuged (3,000 rpm×10 min., 20° C.). The hexane layer (4.0 ml) was evaporated to dryness, and the residue was dissolved in ethanol (100 $\mu$l). The sample thus prepared was determined on the MK-7 content ($\mu$g/g dried sample) by the HPLC method in the same manner as in EXAMPLE 1. As a result, it was shown that the MK-7 contents of the samples were 2,800, 2,200 and 2,000 $\mu$g/g dried sample for the samples which had been adjusted to pH 1.02, 2.07 and 3.01, respectively.

A solution of each of the freeze-dried products (15 mg) in distilled water (5 ml) was centrifuged (10,000 rpm×10 min.). The supernatant (i.e., a water-soluble fraction) was determined on the MK-7 derivative content in the same manner as above. As a result, it was shown that the MK-7 derivative contents of the samples were 1,500, 1,800 and 1,800 $\mu$g/g dried sample for the samples which had been adjusted to pH 1.02, 2.07 and 3.01, respectively, in which the solubilization rates of the water-soluble fractions were about 54%, about 82% and about 90%, respectively. Industrial Applicability Yunnan strain SL-001 of the present invention is capable of producing vitamin K or a derivative thereof with good efficiency.

Yunnan strain SL-001 of the present invention is highly safe, because the strain is isolated from a food. Accordingly, a culture or culture broth of Yunnan strain SL-001 of the present invention in itself can be used as a food additive or a food.

Vitamin K or a derivative thereof prepared from the culture or culture broth of Yunnan strain SL-001 of the present invention is also highly safe, because Yunnan strain SL-001 utilizes foods as sources and therefore a culture or culture broth is also safe. Accordingly, the vitamin K or derivative thereof prepared from the culture or culture broth of Yunnan strain SL-001 of the present invention in itself can also be used as a food additive or a food. In addition to the aforementioned advantages, Yunnan strain SL-001 of the present invention has such an advantage that it can produce a water-soluble vitamin K derivative in high yield as well as a fat-soluble vitamin K. Therefore, wider range of applicability can be expected for the strain.

What is claimed is:

1. An isolated Yunnan strain SL-001 FERM BP-6713 belonging to *Bacillus subtillis*.

2. An isolated Yunnan strain SL-001 FERM BP-6713 belonging to *Bacillus subtillis* according to claim 1, wherein the Yunnan strain is cultivated within a temperature range of from about 20° C. to about 45° C. in a culture medium having a pH in the range of from about 6.0 to about 9.5.

3. An isolated Yunnan strain SL-001 FERM BP-6713 belonging to *Bacillus subtillis* according to claim 2, wherein the Yunnan strain is cultivated within a temperature range of from about 37° C. to about 42° C. in a culture medium having a pH in the range of from about 7.0 to about 8.5.

4. A method of isolating a vitamin K component from Yunnan strain SL-001 which comprises the steps of:
   a) collecting cells of Yunnan strain SL-001;
   b) disrupting the cells so that they release a vitamin K component; and
   c) isolating the released vitamin K component from the disrupted cells.

5. A method of isolating a vitamin K component according to claim 4, wherein the vitamin K component comprises a water soluble vitamin K complex.

6. A method of isolating a vitamin K component according to claim 4, wherein step a) comprises filtering or centrifuging the Yunnan strain cells.

7. A method of isolating a vitamin K component according to claim 4, wherein step b) comprises subjecting the cells to at least one of a chemical treatment and a physical treatment.

8. A method of isolating a vitamin K component from Yunnan strain SL-001 which comprises the steps of:
   a) extracting a fat-soluble fraction from cells of Yunnan strain SL-001;
   b) diluting the fat-soluble fraction with an organic solvent;
   c) mixing the diluted fat-soluble fraction with water and an alcohol;
   d) adding an organic solvent to the mixture of step c);
   e) centrifuging the mixture from step d) to obtain a supernate;
   f) drying the supernate to form a residue;
   g) dissolving the residue from step f) in an alcohol to obtain an isolated vitamin K component.

9. A method of isolating a vitamin K component according to claim 8, wherein the alcohol used in step c) comprises isopropanol.

10. A method of isolating a vitamin K component according to claim 8, wherein the alcohol used in step g) comprises ethanol.

11. A method of isolating a vitamin K component from Yunnan strain SL-001 which comprises the steps of:
   a) providing cells of Yunnan strain SL-001;
   b) adjusting a pH of the Yunnan cells to obtain a precipitate; and
   c) separating a water soluble vitamin K compound from the precipitate.

* * * * *